United States Patent
Yokoi et al.

(10) Patent No.: US 6,825,000 B1
(45) Date of Patent: Nov. 30, 2004

(54) IMMUNOASSAY REAGENT AND IMMUNOASSAY METHOD

(75) Inventors: Masayuki Yokoi, Kusatsu (JP); Takayuki Akamine, Takatsuki (JP); Katsumi Yoshikawa, Hirakata (JP)

(73) Assignee: Sekisui Chemical Co., Ltd., Osaka (JP)

( * ) Notice: Subject to any disclaimer, the term of this patent is extended or adjusted under 35 U.S.C. 154(b) by 0 days.

(21) Appl. No.: 09/673,643

(22) PCT Filed: May 12, 1999

(86) PCT No.: PCT/JP99/02442

§ 371 (c)(1), (2), (4) Date: Oct. 31, 2000

(87) PCT Pub. No.: WO99/60401

PCT Pub. Date: Nov. 25, 1999

(30) Foreign Application Priority Data

| May 15, 1998 | (JP) | ............................................. | 10-133995 |
| Dec. 24, 1998 | (JP) | ............................................. | 10-366818 |
| Dec. 24, 1998 | (JP) | ............................................. | 10-366819 |
| Dec. 24, 1998 | (JP) | ............................................. | 10-366820 |

(51) Int. Cl.[7] .................... G01N 33/543; G01N 33/544; G01N 33/553; G01N 33/554; G01N 33/577

(52) U.S. Cl. .................... 435/7.92; 435/7.71; 435/7.93; 435/40.5; 435/175; 435/177; 435/180; 435/964; 435/973; 435/975; 436/518; 436/519; 436/520; 436/526; 436/528; 436/548; 530/388.26; 530/391.1; 530/815

(58) Field of Search ............................... 435/7.71, 7.92, 435/7.93, 7.94, 40.5, 175, 177, 180, 964, 973, 975; 436/518, 519, 520, 526, 528, 548; 530/388.26, 391.1, 810, 813, 815

(56) References Cited

U.S. PATENT DOCUMENTS

| 4,134,792 A | * | 1/1979 | Boguslaski et al. |
| 4,193,983 A | * | 3/1980 | Ullman et al. |
| 4,582,792 A | * | 4/1986 | Kasahara et al. |
| 4,621,048 A | * | 11/1986 | Ashihara et al. |
| 4,649,105 A | * | 3/1987 | Kasahara et al. |
| 4,868,106 A | * | 9/1989 | Ito et al. |

FOREIGN PATENT DOCUMENTS

| JP | 1214760 | 9/1989 |
| JP | 3167475 | 7/1991 |
| JP | 534346 | 2/1993 |
| WO | WO 8805540 A | 7/1988 |

OTHER PUBLICATIONS

Grunow Roland, et al., "A Cell Surface ELISA For Screening of Monoclonal antibodies to Antigens on Viable Cells in Suspension", Journal of Immunological Methods, vol. 171, No. 1, pp93–102, XP009011105.

Database WPI, XP002242818.

* cited by examiner

Primary Examiner—Christopher L. Chin
Assistant Examiner—James L. Grun
(74) Attorney, Agent, or Firm—Townsend & Banta

(57) ABSTRACT

An immunoassay reagent is obtained whereby a microscale substance such as an antigen or antibody can be assayed at a high sensitivity, and whereby a need to separate a reacted substance, e.g., an immunoreacted substance, from an unreacted substance can be eliminated or such a separation can be simplified.

An immunoassay reagent, for use in the quantitative determination of a target antigen or antibody present in a sample, containing an insoluble carrier which carries an enzyme and an antibody or antigen corresponding to the antigen or antibody, an enzyme inhibitor for inhibiting the activity of the enzyme and a substrate with which the enzyme reacts.

11 Claims, 1 Drawing Sheet

US 6,825,000 B1

IMMUNOASSAY REAGENT AND IMMUNOASSAY METHOD

TECHNICAL FIELD

The present invention relates to an immunoassay reagent utilizing an insoluble carrier and an immunoassay method, and more particularly to an immunoassay reagent and an immunoassay method capable of high-sensitive detection of a target substance in a subject.

BACKGROUND ART

In the field of clinical testing, diagnoses of diseases are carried out using biosamples (such as blood and urine). For these diagnoses, a variety of assays have been developed and utilized. Typical assays include biochemical assays such as utilizing an enzyme reaction, and immunoassays such as utilizing an antigen-antibody reaction. The recent demand to perform precise assaying of components present in biosamples has led to the wide-spread use of immunoassay methods utilizing highly-specific antigen-antibody reactions.

Examples of immunoassay methods include immunoturbidimetry (TIA method), latex immunoassay (LIA method), enzyme immunoassay (EIA method) and radioimmunoassay (RIA method). Selection is made depending upon the particular purpose contemplated. That is, the TIA or LIA method may be employed when a biosample contains a target substance in a relatively large quantity. The TIA and LIA methods are generally employed to assay a substance, such as C-reactive protein (CRP), anti-streptolysin O antibody (ASO) or fibrin degradation product (FDP), particularly when it is contained in a biosample in concentrations of not below several ng/ml. On the other hand, the EIA or RIA method may be used when a biosample contains a target substance in a relatively small quantity. These TIA and LIA methods are generally employed in assaying substances, such as cancer markers represented by α-fetoprotein (AFP) and hormones represented by insulin, particularly when they are contained in a biosample in concentrations of not above several ng/ml.

The recent trend of placing greater importance on assay of microscale substances in a biosample further increases frequencies in use of EIA and RIA methods. In contrast to the TIA and LIA methods which can enjoy shortend testing time and simplified operation and find applications to various types of autoanalyzers (hereinafter referred to as clinical chemistry autoanalyzers), the EIA and RIA methods suffer from the following dificiencies: they need prolonged reaction periods; they require complex operations; and they employ diverse enzymes and radioisotopes. Because of these dificiencies, the EIA and RIA methods are frequently limited to use with specific autoanlyzers (hereinafter referred to as specialized autoanalyzers). The RIA method further requires special facilities because of its utilization of radioisotopes.

A need has arisen for a technique which allows assaying of ultramicro-scale substances in a biosample to thereby enable early detection of cancers and early diagnosis of infection with AIDS virus. There are two groups of techniques which have been found to enable assaying of ultramicro-scale substances. One group of techniques is directed to increase precisions of conventional assay methods, including modifications and improvements of the LIA and EIA methods. Another group of techniques is directed to improve performances of conventional devices used for the LIA and EIA methods. Some of such techniques have been put into practice.

Examples of techniques contemplated to increase the precision of assay methods themselves include a technique which colors insoluble carriers for use in the LIA method (Japanese Patent Laying-Open No. Hei 1-214760) and a technique which utilizes fluorescent materials, instead of enzymes, for labeling antigens or antibodies for use in the EIA method (Japanese Patent Laying-Open No. Hei 5-34346). Also, examples of techniques contemplated to improve performances of deviced include a technique proposed in Japanese Patent Laying-Open No. Hei 3-167475.

However, neither of these techniques are applicable to clinical chemistry autoanalyzers and the problem of requiring specialized autoanalyzers remains unsolved. The need of such specialized autoanalyzers arises because the reaction time, procedure and type of enzyme or radioisotope for use in micro-scale assay methods, as represented by the EIA and RIA methods, are varied depending upon the particular method used, as stated earlier. Other major reason is based on the fact that the micro-scale assays as currently developed or heretofore marketed always require an operation called B/F separation (B is a bound component via an immune reaction and F is a free component). This makes them unapplicable to clinical chemistry autoanalyzers incapable of B/F separation and necessitates specialized autoanalyzers capable of B/F separation.

Assay methods which do not require B/F separation have been recently proposed and developed, as seen in Japanese Patent Laying-Open Nos. Hei 5-249112 and Hei 7-179495. Due to the insufficient sensitivity and extended determination period, they in some cases require specialized autoanalyzers and in other cases find a limited application to clinical chemistry autoanalyzers, which have been problems.

In order to perform ultramicro-scale analysis in the scene of actual clinical examinations, it is required to purchase an expensive special autoanalyzer and secure a place for its installation. There accordingly remains a strong demand for a method which can assay ultramicro-scale substances with the use of clinical chemistry autoanalyzers.

As stated above, the methods currently developed or marketed for assaying ultramicro-scale substances require the B/F separation, as against such a strong demand from users. This presents a major problem, i.e., their practices are limited on special autoanalyzers.

In the scene of clinical examinations, it is frequent to test several items using a single biosample. In such an instance, the single biosample is repeatedly subjected to different assay methods. This not only prolongs the time necessary to complete the testing, but also increases a chance for a tester to contact the biosample and thereby increases a risk of infection, which have been problems.

SUMMARY OF THE INVENTION

It is an object of the present invention to provide an immunoassay reagent and an immunoassay method which can solve the above-described problems, which can assay an ultramicro-scale substance in a sample, such as an antigen or antibody, with a high level of sensitivity, and which can either eliminate the need to carry out the B/F separation or simplify the B/F separation in assaying ultramicro-scale substances.

A first invention of the present application is an immunoassay reagent for quantitatively determining a target material, i.e., an antigen or antibody in a sample, which is characterized as containing (a) an insoluble carrier for carrying an enzyme and an antibody or antigen corresponding to the aforementioned antigen or antibody, the aforementioned insoluble carrier comprising at least one selected from the group consisting of an organic polymer powder particle, microorganism, blood cell and cell membrane fragment, (b) an enzyme inhibitor for inhibiting the activity of the aforementioned enzyme and (c) a substrate with which the aforementioned enzyme reacts.

In a particular aspect of the first invention, there are provided a first reagent containing the aforementioned insoluble carrier and a second reagent containing the aforementioned enzyme inhibitor and substrate.

A second invention of the present application is an immunoassay reagent for quantitively determining a target material, i.e., an antigen or antibody in a sample, which is characterized as containing (a) an insoluble carrier for carrying an enzyme inhibitor and an antibody or antigen corresponding to the aforementioned antigen or antibody, the aforementioned insoluble carrier comprising at least one selected from the group consisting of an organic polymer powder particle, microorganism, blood cell and cell membrane fragment, (b) an enzyme whose activity is inhibited by the aforementioned enzyme inhibitor and (c) a substrate with which the aforementioned enzyme reacts.

In a particular aspect of the immunoassay reagent in accordance with the second invention, there are provided a first reagent containing the aforementioned insoluble carrier, a second reagent containing the aforementioned enzyme and a third reagent containing the aforementioned substrate.

For the immunoassay reagents in accordance with the first and second inventions, a magnetic or magnetizable material is preferably incorporated in the insoluble carrier.

Also in the immunoassay reagents in accordance with the first and second inventions, the aforementioned antibody or antigen, enzyme inhibitor and enzyme can be used in several combinations whereby several types of antigens or antibodies can be quantitatively determined.

A third invention of the present application is an immunoassay reagent for quantitively determining a target material, i.e., an antigen or antibody in a sample, which is characterized as containing (a) an antibody or antigen corresponding to the aforementioned antigen or antibody and chemically coupled to an enzyme inhibitor, (b) an enzyme whose activity is inhibited by the aforementioned enzyme inhibitor and (c) a substrate with which the aforementioned enzyme reacts.

In a particular aspect of the third invention, there are provided a first reagent containing the aforementioned antibody or antigen chemically coupled to the enzyme inhibitor, a second reagent containing the aforementioned enzyme and a third reagent containing the aforementioned substrate.

In a particular aspect of the immunoassay reagent in accordance with the first, second or third inventions, an antibody against the enzyme is used as the enzyme inhibitor. In a more particular aspect, a monoclonal antibody is used.

A fourth invention of the present application is an immunoassay method utilizing the immunoassay reagent in accordance with the first, second or third invention. In this immunoassay method, a sample containing an antigen or antibody as a target material is mixed with the immunoassay reagent in accordance with the first, second or third invention, so that an agglutination reaction in the form of a antigen-antibody reaction and an enzyme reaction are caused to occur. The antigen or antibody can be quantitated by measuring the degrees of such reactions caused.

DETAILED DESCRIPTION OF THE INVENTION

The first invention provides an immunoassay reagent which contains (a) an insoluble carrier that carries an enzyme and an antibody or antigen, (b) an enzyme inhibitor and (c) a substrate. Mixing of these components, prior to use, may cause an enzyme-substrate reaction to proceed or allow the enzyme inhibitor to deactivate the enzyme. Thus, the immunoassay reagent in its general form comprises two separate reagents; a first reagent containing the insoluble carrier (a) and a second reagent containing the enzyme inhibitor and substrate.

The below-described first and second reactions are caused to proceed when the first reagent containing the insoluble carrier that carries an enzyme and an antibody or antigen corresponding to the antigen or antibody as a target material in a sample, together with the second reagent containing a substance for inhibiting the activity of the enzyme (hereinafter referred to as an enzyme inhibitor) and the substrate with which the enzyme reacts, are mixed with a biosample containing the above-specified target material. The first reaction is an antigen-antibody reaction of the antigen or antibody present in the biosample with the corresponding antibody or antigen carried by the insoluble carrier. The first reaction is similar in principle to the LIA method and results in the agglutination of the insoluble carriers, whereby the mixture is increased in turbidity to change its light absorbence. On the other hand, the second reaction is a reaction between the enzyme and substrate and is similar in principle to the EIA. The absorbence of mixture is varied as the substrate undergoes a change.

Since the first and second reactions are caused to occur almost concurrently but independently, the degree of change in absorbence of the mixture is increased compared to the LIA method. This enables assaying of micro-scale substances present in a biosample. However, while the first reaction undergoes a change in absorbence with the amount of antigen or antibody present in the biosample, the second reaction is independent of the amount of antigen or antibody in the biosample because it is an enzyme-substrate reaction.

The inventors of the present application have found from their intensive researches that the inclusion of enzyme inhibitor in a reaction system induces the second reaction to depend upon the the amount of antigen or antibody present in the biosample. The enzyme inhibitor, when coupled to an enzyme, renders the enzyme inactive or less active. In the absence of the antigen or antibody in the biosample, the aggregation of insoluble carriers, via the first reaction, does not take place. The enzyme inhibitor is then allowed to bind to the enzyme on the insoluble carrier to render it inactive, so that the absorbence becomes unaffected by the second reaction. In contrast, in the presence of the antigen or antibody in the biosample, the first reaction results in the aggregation of insoluble carriers. In such an instance, a steric hindrance of the resulting aggregates reduces the occurrence of the enzyme inhibitor to bind to the enzyme on the insoluble carriers that participate in the aggregation. The enzyme is thus prevented from being deactivated and allowed to react with the substrate, thereby causing the change in absorbence.

In the fashion as stated above, the inclusion of the enzyme inhibitor in the reaction system renders the second reaction dependent upon the amount of antigen or antibody present in the biosample. Because the first and second reactions are both made dependent upon the amount of antigen or antibody present in the biosample, the immunoassay method in accordance with the first invention shows the increased sensitivity relative to the LIA method. Unlike the EIA method, it does not require the B/F separation or may be accompanied by the simplified B/F separation.

In the second invention, an immunoassay reagent is used which contains (a) an insoluble carrier that carries an antigen or antibody and an enzyme inhibitor, (b) an enzyme and (c) a substrate. Like the first invention, pre-mixing of these components may cause an enzyme-substrate reaction to proceed or the enzyme to deactivate.

Hence, the immunoassay reagent of the second invention in its general form comprises a first reagent containing the insoluble carrier, a second reagent containing the enzyme and a third reagent containing the substrate. In such a general form, if the first reagent is mixed with a biosample containing the above-specified target material, an antigen-antibody reaction (first reaction) is caused to occur between the antigen or antibody present in the biosample and the antibody or antigen carried by the insoluble carrier, resulting in aggregation of the insoluble carriers. When the second reagent is subsequently added, a reaction (second reaction) is caused to occur between the enzyme in the second reagent and the enzyme inhibitor supported by the insoluble carrier. This second reaction is dependent upon the amount of the antigen or antibody in the biosample. The enzyme, when reacted with the enzyme inhibitor, lose or reduce its activity. In the absence of the antigen or antibody in the biosample, the aggregation of the insoluble carriers via the first reaction does not occur. The enzyme inhibitor carried on the insoluble carrier is then allowed to attack the enzyme to render it inactive. Thus, the subsequent addition of the third reagent does not induce the absorbence change via the second reaction.

By contrast, in the presence of the antigen or antibody in the biosample, the insoluble carriers are caused to aggregate via the first reaction to the extent that depends upon the content of the antigen or antibody. In such a case, a steric hindrance of the resulting aggregates reduces the occurrence of the reaction between the enzyme and the enzyme inhibitor on the insoluble carrier. The enzyme is accordingly prevented from being deactivated. Therefore, when the third reagent is subsequently added, the enzyme is allowed to react with the substrate, whereby the absorbence is changed.

In the manner as stated above, the configuration of the insoluble carrier to support the enzyme inhibitor is also effective to render the second reaction dependent upon the amount of the antigen or antibody present in the biosample. Also in accordance with the immunoassay reagent and method of the second invention, the first and second reactions are both rendered dependent upon the amount of antigen or antibody present in the biosample.

Like the first invention, the immunoassay reagent and method can be obtained which have the increased sensitivity relative to the LIA method and which, unlike the EIA method, do not require the B/F separation or may be accompanied by the simplified B/F separation.

The immunoassay reagent in accordance with the first or second invention may further include a magnetic material or magnetizable material incorporated in the insoluble carrier. In the case where such a magnetic or magnetizable material is incorporated in the insoluble carrier, the insoluble carrier can be separated from the solution by operating an external magnet or magnetizable substance, after completion of all the reactions, so as to magnetically attract the insoluble carrier from a bottom portion of a reactor. This allows measurement in color of the solution only, without being affected by the increase in turbidity of the insoluble carrier.

Also for the immunoassay reagent in accordance with the first or second invention, the aforementioned antibody or antigen, enzyme inhibitor and enzyme may be used in several combinations whereby several types of antigens or antibodies can be quantitatively determined.

Also in the case where a magnetic or magnetizable material is included in the insoluble carrier and where the antibody or antigen, enzyme and enzyme inhibitor are used in several different combinations, the colors of individual enzymes only can be measured without being affected by a turbidity increase resulting from aggregation of the insoluble carriers. This allows simultaneous measurement of two or more types of antigens or antibodies.

The immunoassay reagent of the first invention does not necessarily comprise the aforementioned first and second reagents. Likewise, the immunoassay reagent of the second invention does not necessarily comprise the aforementioned first, second and third reagents. For the immunoassay reagent of the first invention, the aforementioned insoluble carrier (a), enzyme inhibitor (b) and substrate (c) may be mixed simultaneously and then added to a sample to be tested without delay, for example. Likewise, all the ingredients of the immunoassay reagent according to the second invention may be mixed simultaneously and then added to a sample to be tested without delay. As such, if conditions are properly set, the immunoassay reagent according to the first or second invention does not necessarily take the form of consisting of the separately-prepared first and second reagents or the separately-prepared first, second and third reagents.

In the immunoassay reagent according to the third invention, an enzyme inhibitor is chemically bound to an antibody or antigen. The first reaction is initially caused to occur. That is, when a biosample is mixed with the antibody or antigen (hereinafter referred to as a conjugate) corresponding to a target antigen or antibody present in the sample and chemically bound to the enzyme inhibitor, an agglutination reaction is caused to occur between the antibody or antigen and the antigen or antibody present in the biosample. This agglutination reaction results in creating a steric hindrance or changing a conformation of the enzyme inhibitor in the conjugate, whereby the enzyme inhibitor is rendered inactive and accordingly the enzyme inhibiting action is weakened. That is, the enzyme inhibiting action is weakened depending upon the level of agglutination via the antigen-antibody reaction.

As the second reaction is then caused to proceed, the enzyme inhibitor, according to its activity, restricts the action of enzyme so that the enzyme present in a system is deactivated to the extent that depends upon the activity of the enzyme inhibitor.

When the enzyme is finally allowed to react with the substrate, color emission occurs as the third reaction. By measuring the degree of such color emission, the degree of activity loss of the enzyme can be detected. That is, the degree of agglutination can be detected by finally measuring the enzyme activity from the substrate.

Summarizing the precedings, the occurrencce of an agglutination reaction, i.e., the antigen-antibody reaction between the target material and the conjugate, weakens the enzyme inhibiting action of the enzyme inhibitor that exists in the conjugate. Thereafter, the enzyme is deactivated by the action of enzyme inhibitor to the extent that depends upon the degree of agglutination. By measuring the activity of enzyme with the addition of the substrate, the target material in the system- can be assayed.

As explained above, in accordance with the immunoassay reagent and method of the present invention, the first, second and third reactions are all rendered dependent upon the amount of antigen or antibody present in a biosample. Therefore, they are novel immunoassay reagent and method which exhibit the increased sensitivity relative to the LIA method and which, unlike the EIA method, do not require the B/F separation.

In the preceding descrioptions, the first, second and third reactions are separately explained in three stages for better understanding. However, the reagent for use in the actual measurement is not necessarily divided into three types. If proper conditions are selected, the reagent may be divided into one or two types, or alternatively, into three or more types.

The target materials which can be assayed in the first, second or third invention may be antigens or antibodies contained in a biosample, examples of which include, but not limited to, hepatitis (B, C)-derived antigens or antibodies; HIV antigens or antibodies; syphilis-derived antigens or antibodies; cancer markers represented by α-fetoprotein; hormones represented by insulin; autacoids and the like.

Examples of insoluble carriers for use in the first or second invention include powder-form organic polymers, microorganisms, blood cells, cell membrane fragments and the like. Examples of powder-form organic polymers, include powder-form natural polymers such as insoluble agarose, cellulose and insoluble dextran; powder-form synthetic polymers such as polystyrene, styrene-styrene sulfonic acid (sulfonate) copolymer, styrene-methacrylic acid copolymer, acrylonitrile-butadiene-styrene copolymer, vinyl chloride-acrylate copolymer, vinyl acetate-acrylate copolymer and the like. Particularly preferred is a latex in which synthetic polymer particles are uniformly suspended. While varied in type depending upon the particular end purpose and use contemplated, the insoluble carrier is generally produced by chemical synthesis or commercially avialable. Also suitable is the insoluble carrier having a sulfonic- or carboxyl-introduced surface. The latex, if used, preferably contains particles having sizes in the range of 0.05–1.5 µm, more preferably in the range of 0.1–0.6 µm.

In the first or second invention, a magnetic or magnetizable material may be incorporated in the insoluble carrier. Illustrative of the magnetic material is ferrite and illustrative of the magnetizable materials is iron oxide. A specific example of the magnetizable material-containing insoluble carrier is a product manufactured by Belytus Co., Ltd. and designated in trade as DYNABEADS.

The enzyme for use in the immunoassay reagent according to the first, second or third inventions is not particularly specified, so long as its reaction with a substrate results in the change in absorbency. Examples of enzymes include, but not limited to, peroxidase, alkaline phosphatase, β-galactosidase and the like. Enzymes obtained either from natural sources or by a gene engineering technique are useful. In general, those obtained from natrual sources may be used conveniently.

The enzyme when in use for measurement may be diluted with a suitable buffer. Examples of buffers include, but not limited to, phosphate, tris, glycine and Good's buffers. The type of the buffer may be suitably chosen depending upon the properties of the enzyme and substrate used. The enzyme when in use may preferably be adjusted to a concentration range of 0.001–10 IU/mL. However, such a range may be varied depending upon the particular type of the enzyme used.

The substrate for use in the immunoassay reagent according to the first, second or third inventions is a substance which provides an absorbency change when reacted with the enzyme used. In an exemplary case where peroxidase is used as the enzyme, a suitable substrate may be an aqueous hydrogen peroxide to which N-ethyl-N-(2-hydroxy-3-sulfopropyl)-3,5-dimethoxyaniline, o-phenylenediamine or pyrogallol is added. In another exemplary case where alkaline phosphatase is used as the enzyme, a suitable substrate may be p-nitrophenyl phosphate. In still another exemplary case where β-galactosidase is used as the enzyme, a suitable substrate is o-nitrophenyl-β-D-galactopyranoside. However, the substrate is not particularly specified in type and may be suitably chosen depending upon the particular purpose and use contemplated.

In general, the aforementioned substrates are either manufactured by chemical synthesis or available from the market. The substrate when in use for measurement is dissolved in or diluted with a suitable buffer. Examples of buffers include, but not limited to, phosphate, tris, glycine and Good's buffers. The type of the buffer used may be suitably chosen depending upon the properties of the enzyme and substrate used. The substrate when in use may preferably be adjusted to-a concentration range of 0.1–1,000 mM. Such a range may however be varied depending upon the particular type of the substrate used.

The enzyme inhibitor for use in the immunoassay reagent according to the first, second or third inventions is not particularly specified, so long as it is able to couple to the enzyme used so that the enzyme is rendered inactive. Examples of useful enzyme inhibitors include peptides, antibodies, fluorine compounds, sulfur compounds and the like. The enzyme inhibitor may be suitably chosen depending upon the particular type of the enzyme used.

Where an antibody to the enzyme (hereinafter referred to as the anti-enzyme antibody) is used as the enzyme inhibitor, such an antibody may be either polyclonal or monoclonal in type and can be manufactured by any known technique. The anti-enzyme antibody, if polyclonal, can be immune produced from the enzyme introduced into an animal such as a rabit, goat or sheep. In the similar manner, the monoclonal antibody can also be produced by using any known technique.

The antibody such obtained may be suitably purified as by a known chromatography. If circumstances permit, it may be used without being subjected to special purification. The anti-enzyme antibody when in use for measurement is diluted as with a suitable buffer. Examples of buffers include, but not limited to, phosphate, tris, glycine and Good's buffers. The buffer may be suitably chosen depending upon the properties of the enzyme and substrate used.

The enzyme inhibitor when in use may preferably be adjusted to a concentration range of 0.01–10 mg/mL. Such a range may however be varied depending upon the particular type of the enzyme inhibitor used.

The following describes a procedure which can be utilized to prepare the insoluble carrier (a) for use in the first invention, which carries an enzyme and an antibody or antigen corresponding to an antigen or antibody present in a biosample.

While varied depending upon the particular types of the enzyme and antibody or antigen used, the following technique is generally utilized to bind the antibody or antigen and enzyme to the insoluble carrier. A solution containing the antibody or antigen and a solution containing the enzyme are added simultaneously or sequentially to a suspension of insoluble carriers. The subsequent stirring causes the antibody or antigen and enzyme to bind to the insoluble carriers by physical adsorption.

In the case of insoluble carriers having a sulfonic- or carboxyl-introduced surface, the antibody or antigen and enzyme can be bound thereto by the addition of a suitable crosslinking agent. In this case, the antibody or antigen and enzyme must be chemically modified so that crosslinking can be achieved by a crosslinking agent. Considering the properties and structures of the antibody or antigen and enzyme used, a technique may be suitably selected whereby they are caused to physically adsorb or bind to the insoluble carriers with the aid of crosslinking agent.

The above-described binding reaction is preferably carried out in the pH range of 3–10 at a temperature of 2–50° C. If the pH falls outside the specified range, a problem may arise, e.g., the antibody or antigen may undergo a change in property as it is a protein. If the reaction temperature falls below 2° C., the reaction rate may become slow to result in the difficulty to obtain a product having a desired level of sensitivity. If the reaction temperature goes beyond 50° C., a problem such as a property change of the antibody or antigen may arise.

In the preparation of the insoluble carrier (a), the enzyme bound thereto in the first invention is replaced by the enzyme inhibitor in the second invention.

The immunoassay reagent in accordance with the third invention includes the enzyme inhibitor chemically coupled to the antibody or antigen. The following procedure can be utilized to prepare such an enzyme inhibitor chemically coupled to the antibody or antigen.

While varied depending upon the types of the antibody or antigen and enzyme inhibitor, an optimum process whereby the enzyme inhibitor is chemically coupled to the antibody or antigen corresponding to a target antigen or antibody may be suitably chosen from conventionally-known processes. Examples of applicable processes include a mixed acid anhydride process wherein a carboxyl group is caused to react with ethyl chlorocarbonate or butyl chlorocarbonate to thereby derive active mixed acid anhydride which is subsequently reacted with an amino group of the other to form an amide bond; an active ester process wherein a carbodiimide-based condensing agent is used to convert a carboxyl group to an active ester form which is subsequently caused to react with an amino group of the other; a process utilizing glutaric aldehyde; a process utilizing periodic acid and the like. In the case where a polyclonal or monoclonal antibody is used as the enzyme inhibitor, a binding ratio of the antibody or antigen used to the enzyme inhibitor, (antibody or antigen) :(enzyme inhibitor)=preferably 20:1–1:1, more preferably 10:1–1:1, still more preferably 5:1–1:1.

In accordance with the immunoassay method of the present invention, the immunoassay reagent according to the first, second or third invention is mixed with a test sample containing an antigen or antibody to cause an agglutination reaction as one type of an antigen-antibody reaction and an enzyme reaction. The antigen or antibody can be quantitated by measuring the degrees of these reactions.

While not limiting, a method which involves detecting optical properties of reaction products is generally utilized to measure such degrees of reactions. The most popular optical detection method involves detecting a change in color hue in response to light absorption. Other useful methods utilize fluorescence, chemiluminescence and bioluminescence. The optical measurement method is not particularly specified and may be suitably chosen depending upon the purpose and use contemplated. Examples include wavelength measurement, time-resolved fluorescence method and the like.

In the wavelength measurement, a useful wavelength typically falls within the approximate range of 250–1,000 nm. In this measurement method, an antigen-antibody reaction and an enzyme reaction are carried out under ordinary conditions. Various buffers can be used as a reaction medium. Any type of buffer can be used, so long as it has such ionic strength and pH that neither deactivate an antigen or antibody present in a biosample nor inhibit the antigen-antibody reaction and enzyme reaction. Examples of useful buffers include phosphate, tris and glycine buffers. A reaction temperature is preferably in the range of 10–50° C., more preferably in the range of 20–40° C.

DESCRIPTION OF EXAMPLES

Example 1

(1) Preparation of an Immunoassay Reagent

50 μl of a solution containing 1 mg anti-human HBs antigen goat antibody/ml of a phosphate buffer (pH 5.0, 50 mM) and 50 μl of a solution containing 1 mg horseradish peroxidase/ml of a phosphate buffer (pH 5.0, 50 mM) were added to 1 ml of a 0.02 wt. % dispersion of polystyrene latex (particle size of 0.4 μm, product of Sekisui Chemical Co., Ltd.) in a phosphate buffer (pH 5.0, 50 mM) stored at 25° C. The mixture was stirred for 1 hour at 25° C.

The mixture was then centrifuged at 15,000 rpm for 15 minutes. After removal of a supernatant, a resultant precipitate was dispersed in 1 ml of a phosphate buffer (pH 5.0, 50 mM) to prepare a first reagent.

1 ml of an anti-horseradish peroxidase monoclonal antibody solution at a concentration of 0.4 mg/ml, 1 ml of an N-ethyl-N-(2-hydroxy-3-sulfopropyl)-3,5-dimethoxyaniline solution at a concentration of 1 mg/ml, 1 ml of a 2 mM 4-aminoantipyrine solution, and 1.2 ml of a 10 mM hydrogen peroxide solution were added to 10 ml of a phosphate buffer (pH 7.0, 50 mM) to prepare a second reagent.

That is, the immunoassay reagent of this Example consisted of the aforementioned first and second reagents.
(2) By utilizing this immunoassay reagent, a standard HBs antigen calibration curve was drawn. Subsequently, an HBs antigen positive serum was used as a specimen to measure a titer of HBs antigen contained therein.

(2-1) Standard HBs Antigen

A human serum containing an HBs antigen at a concentration of 0, 10, 25, 50, 75 or 100 I.U./ml was used as a standard solution.

(2-2) Calibration Curve Preparation

Figure 1:
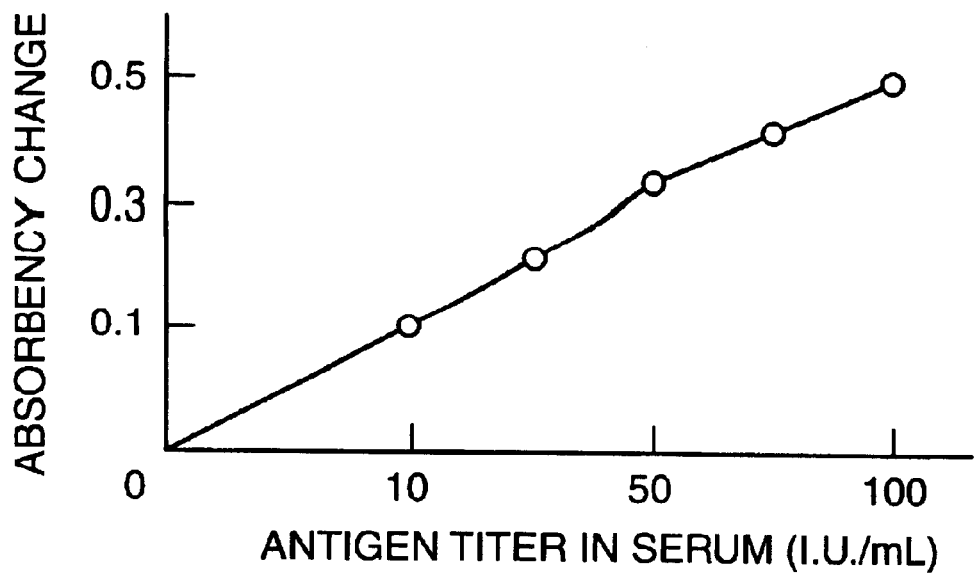
FIG. 1 is a calibration curve obtained from Example 1 wherein an ordinate axis indicates a variation of absorbency at 600 nm and an abscissa axis indicates a titer (I.U./ml) of an HBs antigen in serum.

A Hitachi autoanalyzer, model number 7150, was used to measure absorbency. 20 μl of each standard HBs antigen solution prepared in (2-1) was added to 120 μl of the first reagent to provide a mixture. The mixture was maintained at 37° C. for 10 minutes and subsequently mixed with 120 μl of the second reagent. The absorbency at a wavelength of 600 nm was measured after 1 and 10 minutes. The difference was reported as an absorbency change. A standard HBs antigen titer vs. absorbency change calibration curve was shown in FIG. 1. In FIG. 1, an ordinate axis indicates an absorbency change at 600 nm and an abcissa axis indicates a titer (I.U./ml) of an HBs antigen in a serum.

(2-3) HBs Antigen Positive Serum Testing

The procedure of the calibration curve preparation section (2-2) was repeated, except that 20 µl of standard HBs antigen solution used therein was changed to 20 µl of an HBs antigen positive serum, to find an absorbency change. By applying the value obtained for absorbency change onto the calibration curve, a titer of HBs antigen in the HBs antigen positive serum was determined. 6 different specimens (designated by A, B, C, D, E and F) were used for the HBs antigen positive serum. Measurement of each serum was repeated five times to obtain an average value and a coeffecient of variance (CV) (%). The results are given in Table 1.

TABLE 1

| Designation of Patient | Titer of HBs Antigen in Serum (I.U./ml) | Coefficient of Variation (%) |
| --- | --- | --- |
| A | 8.5 | 7 |
| B | 6.3 | 8 |
| C | 8.9 | 8 |
| D | 10.5 | 4 |
| E | 5.4 | 9 |
| F | 3.2 | 9 |

As can be appreciated from the results shown in Table 1, the immunoassay method according to the present invention allows measurement of serums having titers of not above 10 I.U./ml.

Example 2

(1) Preparation of an Immunoassay Reagent 0.05 mg of anti-human HBs antigen goat antibody and 0.05 mg of horseradish peroxidase were added to 1 ml of a 0.02 wt. % dispersion of polystyrene latex (particle size 0.4 µm, product of Belitus Co., Ltd.) containing magnetizable particles ($Fe_2O_3$) in a phosphate buffer (pH 5.0, 50 mM) stored at 25° C. The mixture was stirred for 1 hour at 25° C.

The mixture was then centrifuged at 15,000 rpm for 15 minutes. After removal of a supernatant, a resultant precipitate was dispersed in 1 ml of a phosphate buffer (pH 5.0, 50 mM) to prepare a reagent A.

0.05 mg of anti-human CRP goat antibody and 0.75 mg of β-galactosidase were added to 1 ml of a 0.02 wt. % dispersion of polystyrene latex (particle size. 0.4 µm, product of Belitus Co., Ltd.) containing magnetizable particles ($Fe_2O_3$) in a phosphate buffer (pH 5.0, 50 mM) stored at 25° C. The mixture was stirred for 1 hour at 25° C.

This mixture was then centrifuged at 15,000 rpm for 15 minutes. After removal of a supernatant, a resultant precipitate was dispersed in 1 ml of a phosphate buffer (pH 5.0, 50 mM) to prepare a reagent B.

The above-prepared reagents A and B were blended in a ratio of 1:1 to provide a first reagent.

1 ml of an anti-horseradish peroxidase monoclonal antibody solution at a concentration of 0.4 mg/ml, 1 ml of an N-ethyl-N-(2-hydroxy-3-sulfopropyl)-3,5-dimethoxyaniline solution at a concentration of 1 mg/ml, 1 ml of a 2 mM 4-aminoantipyrine solution, and 1.2 ml of a 10 mM hydrogen peroxide solution were added to 10 ml of a phosphate buffer (pH 7.0, 50 mM) to prepare a reagent C.

Next, 1 ml of an anti β-galactosidase monoclonal antibody solution at a concentration of 0.4 mg/ml and 0.1 g of o-nitrophenyl-β-D-galactopyranoside were added to 10 ml of a phosphate buffer (pH 7.0, 50 mM) to prepare a reagent D.

The above-prepared reagents C and D were blended in a ratio of 1:1 to provide a second reagent.

That is, the immunoassay reagent of this Example consisted of the aforementioned first and second reagents.

(2) By utilizing this immunoassay reagent, measurement was achieved for a human serum specimen containing both a standard HBs antigen and a standard CRP, so that respective calibration curves with respect to the standard HBs antigen and standard CRP were prepared. Subsequently, an HBs antigen positive and CRP positive serum was used as a specimen and its HBs antigen titer and CRP concentration were measured.

(2-1) Human Serum Specimen Containing Both a Standard HBs Antigen and a Standard CRP Human serum specimens which respectively contained 0 I.U./ml of HBs antigen and 0 mg/dl of standard CRP; 10 I.U./ml of HBs antigen and 1 mg/dl of standard CRP; 25 I.U./ml of HBs antigen and 2.5 mg/dl of standard CRP; 50 I.U./ml of HBs antigen and 5 mg/dl of standard CRP; 75 I.U./ml of HBs antigen and 7.5 mg/dl of standard CRP and 100 I.U./ml of HBs antigen and 10 mg/dl of standard CRP were used as standard solutions.

(2-2). Calibration Curve Preparation

A Hitachi spectrophotometer, model number U-3200, was used to measure absorbency. 20 µl of each human serum specimen containing both the standard HBs antigen and standard CRP prepared in (2-1) was added to 120 µl of the first reagent to provide a mixture. The mixture was maintained at 37° C. for 10 minutes and subsequently mixed with 120 µl of the second reagent. After the lapse of 10 minutes, a magnet was manipulated to attract the insoluble carriers to a bottom of a reactor. The absorbency of a resultant supernatant liquid was measured at 600 nm and 420 nm.

An absorbency change at a wavelength of 600 nm was given by subtracting a value obtained for the serum having a standard HBs antigen concentration of 0 I.U./ml from a value obtained for each standard HBs antigen-containing serum.

An absorbency change at a wavelength of 420 nm was given by subtracting a value obtained for the serum having a standard CRP concentration of 0 mg/dl from a value obtained for each standard CRP-containing serum.

Figure 2:
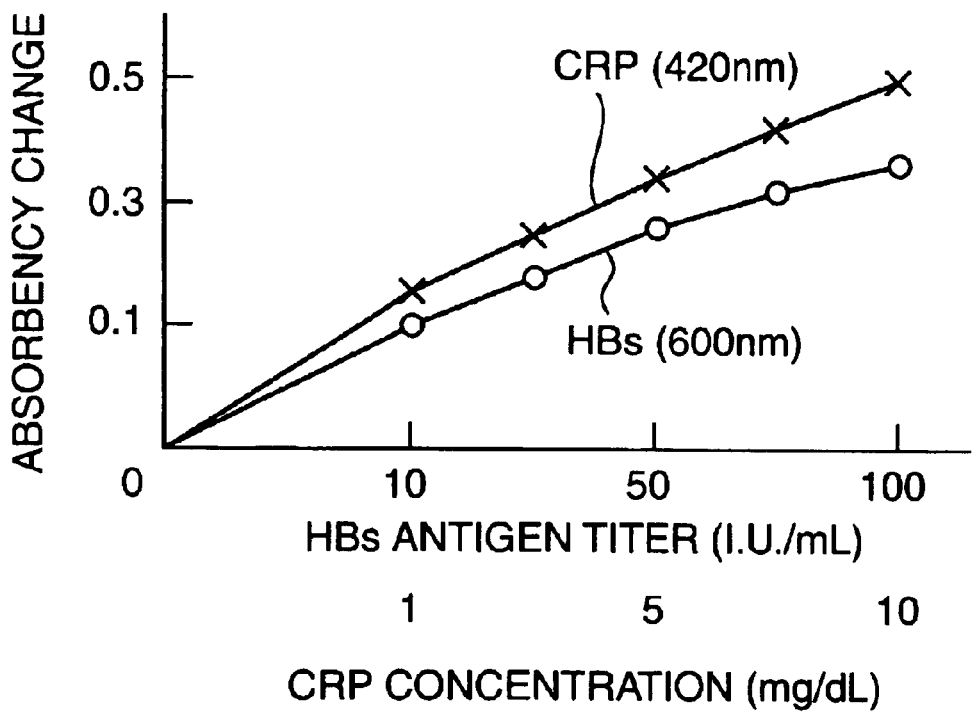
FIG. 2 is a calibration curve obtained from Example 2 wherein an ordinate axis indicates a variation of absorbency at 600 or 420 nm and an abscissa axis indicates an HBs antigen titer (I.U./ml) or a CRP concentration (mg/dl) in serum.

A standard HBs antigen titer vs. absorbency change calibration curve and a standard CRP vs. absorbency change calibration curve were shown in FIG. 2. In FIG. 2, an ordinate axis indicates an absorbency change at 600 nm or 420 nm and an abcissa axis indicates an HBs antigen titer (I.U./ml) or a CRP concentration (mg/dl)of each serum.

(2-3) HBs Antigen Positive and CRP Positive Serum Testing

The procedure of the calibration curve preparation section (2-2) was repeated, except that 20 µl of human serum specimen containing both of the standard HBs antigen and standard CRP was changed to 20 µl of an HBs antigen positive and CRP positive serum, to find an absorbency change. By applying the absorbency change value onto the calibration curves, an HBs antigen titer and a CRP concentration of the HBs antigen positive and CRP positive serum were determined. 6 different specimens (designated by A, B, C, D, E and F) were used for the HBs antigen positive and CRP positive serum. Measurement of each serum was repeated five times to obtain an average value and a coeffecient of variance (CV) (%). The results are given in Tables 2 and 3.

TABLE 2

| Designation of Patient | Titer of HBs Antigen in Serum (I.U./ml) | Coefficient of Variation (%) |
|---|---|---|
| A | 8.5 | 7 |
| B | 6.3 | 8 |
| C | 8.9 | 8 |
| D | 10.5 | 4 |
| E | 5.4 | 9 |
| F | 3.2 | 9 |

TABLE 3

| Designation of Patient | CRP Concentration (mg/dl) | Coefficient of Variation (%) |
|---|---|---|
| A | 0.8 | 10 |
| B | 2 | 8 |
| C | 1 | 4 |
| D | 0.5 | 14 |
| E | 0.4 | 14 |
| F | 0.2 | 18 |

As can be appreciated from the results shown in Tables 2 and 3, the immunoassay method according to the present invention allows the concurrent microscale measurement of a serum having a titer of not above 10 I.U./ml and a CRP antigen concentration.

Example 3

(1) Reagents and Materials

Latex: 10% (W/V) polystyrene latex (particle size of 0.4 μm, product of Sekisui Chemical Co., Ltd.)

Latex diluting buffer: a mixture consisting of 50 mM sodium primary phosphate and 50 mM sodium secondary phosphate and adjusted to a pH of 6.5

Hepatitis C core antigen (p 22): yeast-hosted recombinant hepatitis C core antigen (manufactured by Austral Biologicals Co., Ltd.)

Antigen diluting buffer: identical in type to the aforementioned latex diluting buffer Anti-horseradish peroxidase monoclonal antibody: anti-horseradish peroxide monoclonal antibody precipateted from ascites fluids with the aid of ammonium sulfate and purified to immunoglobulin fractions Antibody diluting buffer: identical in type to the aforementioned latex diluting buffer Enzyme solution (R3 solution): a solution prepared by diluting anti-horseradish peroxidase (257 U/mL, product of Toyobo Co., Ltd.) with the aforementioned latex diluting buffer to a concentration of 0.3 U/mL Substrate solution (R4 solution): a solution prepared by mixing 8 μL of 10 mM N-ethyl-N-(2-hydroxy-3-sulfopropyl)-3,5-dimethoxy aniline (product of Dojin Chemical Co., Ltd.), 40 μL of 4 mM 4-aminoantipyrine (product of Wako Pure Chemical Co., Ltd.) and 3 μL of 12 mM aqueous hydrogen peroxide (product of Minori Chemical Co., Ltd.)

Blocking buffer: the above-specified latex buffer containing 1% (W/V) bovine serum albumin (product of Fraction V. Miles Corp.) and 0.1% (W/V) $NaN_3$ Specimen diluting buffer (R1 solution): the above-specified blocking buffer containing 1% (W/V) polyethylene glycol 6000 (average molecular weight of 7,500, product of Wako Pure Chemical Co., Ltd.)

Hepatitis C virus specimen: hepatitis C virus positive patient's serum (product of Intergen Co., Ltd.)

(2) Preparation of a Latex Reagent 2 parts by volume of latex diluting buffer was added to 1 part by volume of polystyrene latex to obtain a 3.3% (W/V) latex solution. Hepatitis C core antigen and anti-horseradish peroxidase monoclonal antibody were diluted with antigen diluting solution and antibody diluting solution, respectively, each to a protein concentration of 800 μg/mL, to obtain an antigen solution and an antibody solution.

The antigen solution and antibody solution, each in the amount of 100 μL, were added quickly to 300 μL of the above-prepared 3.3% (W/V) latex solution while agitated by a magnetic stirrer in a 25° C. incubator. The mixture was agitated at 25° C. for 1 hour.

0.5 mL of blocking buffer was added to the mixture, followed by one hour of agitation at 25° C. This mixture was then centrifuged at 18,000 rpm at 15° C. for 20 minutes. 20 mL of blocking buffer was added to the resulting precipitate which was subsequently cleaned by the centrifugation under the same conditions as above. The cleaning operation was repeated three times. 2 mL of blocking buffer was added to the cleaned precipitate. After sufficient stirring, the mixture was subjected to a dispersion treatment by an ultrasonic grinder to thereby obtain a 0.25% (W/V) solids latex reagent which was subsequently stored at 4° C.

(3) Measurement Method of Hepatitis C Virus Specimens

The immunoassay reagent of the present invention which comprises the above-prepared latex reagent (an insoluble substance that carries an antigen designated as hepatitis C core antigen and an enzyme inhibitor designated as anti-horseradish peroxidase monoclonal antibody) and the above-specified enzyme solution and substrate solution, in combination with a biochemical autoanalyzer model # 7170 (product of Hitachi Seisakusho Co., Ltd.), was utilized to measure hepatitis C virus specimens according to the following procedure.

The 0.25% (W/V) solids latex reagent obtained in (2) was used as an R2 solution. Measurement was accomplished under the following conditions.

| | |
|---|---|
| Volume of a specimen | 20 μl |
| Specimen diluting solution (R1 solution) | 180 μL |
| Latex reagent (R2 solution) | 20 μl |
| Enzyme solution (R3 solution) | 20 μl |
| Substrate solution (R4 solution) | 20 μl |
| Measurement wavelength | 600 nm |
| Measurement temperature | 37° C. |

A sequence used to introduce the reagents into the specimen loaded cell of the above-specified autoanalyzer comprises introducing R1 solution, R2 solution one minute later, R3 solution four minutes later and R4 solution five minutes later. The difference (ΔOD 600 nm) between absorbencies at about 75 seconds and about 730 seconds after the addition of substrate solution (R4 solution) was measured and multiplied by 10,000. The resulting value was taken as an absorbency change.

(4) Measurement Results

Serum specimens (respectively designated as S-1, S-2, S-3, S-4 and S-5) from five different hepatitis C virus positive patients were diluted by two stages to the degree of $2^{10}$ to provide respective samples. Each sample was measured for absorbency change according to the measurement method described in (3). The results are given in Table 4 wherein the absorbency change is indicated by "+", if equal to or greater than a cutoff value (absorbency change=40), and by "−", if below the cutoff value.

Comparative Example 1

(1) Reagents and Materials

Similar to "(1) Reagents and Materials" described in Example 3.

(2) Preparation of a Latex Reagent

In the "(2) Preparation of a latex reagent" described in Example 3, the hepatitis C core antigen and anti-horseradish peroxidase monoclonal antibody were both carried by the polystyrene latex. However, the anti-horseradish peroxidase monoclonal antibody was not used in this Comparative Example 1. Otherwise, the procedure described in "(2) Preparation of a latex reagent" of Example 3 was followed to prepare a latex reagent carrying the hepatitis C core antigen only.

(3) Measurement Method of Hepatitis C Virus Specimens

The above-prepared latex reagent, in combination with a biochemical autoanalyzer model # 7170 (product of Hitachi Seisakusho Co., Ltd.), was utilized to measure hepatitis C virus specimens according to the following procedure.

The 0.25% (W/V) solids latex reagent obtained in (2) was used as an R2 solution. Measurement was accomplished under the following conditions.

| | |
|---|---|
| Volume of a specimen | 20 μl |
| Specimen diluting solution (R1 solution) | 210 μl |
| Latex reagent (R2 solution) | 30 μl |
| Measurement wavelength | 700 nm |
| Measurement temperature | 37° C. |

A sequence used to introduce the reagents into the specimen loaded cell of the above-specified autoanalyzer comprises introducing R1 solution and R2 solution with a time interval of 5 minutes. The difference (ΔOD 700 nm) between absorbencies at about 55 seconds and about 300 seconds after the addition of latex reagent (R2 solution) was measured and multiplied by 10,000. The resulting value was taken as an absorbency change.

(4) Measurement Results

As similar to Example 3, serum specimens from five different hepatitis C virus positive patients were diluted by two stages to the degree of $2^{10}$ to provide respective samples. Each sample was measured for absorbency change according to the above-described measurement method (3). The results are given in Table 4 wherein the absorbency change is indicated by "+" if equal to or greater than a cutoff value (absorbency-change=80) and by "−" if below the cutoff value.

Comparative Example 2

(1) Reagents and Measurement Method

A commercial EIA kit (HCV EIA II, product of Dynabbot Co., Ltd.) was used as an EIA kit for assaying hepatitis C virus antibody. The antibody present in the specimen was quantitated according to the operating instructions as attached to the kit.

(2) Measurement Results

As similar to Example 3, serum specimens from five different hepatitis C virus positive patients were diluted by two stages to the degree of $2^{10}$ to provide respective samples. Each sample was measured for absorbency change according to the above-described measurement method (2). The results are given in Table 4 wherein the absorbency change is indicated by "+" if equal to or greater than a cutoff value (calculated from absorbencies of positive and negative controls attached to the kit) and by "−" if below the cutoff value.

TABLE 4

| | | Dilution Ratio | | | | | | | |
|---|---|---|---|---|---|---|---|---|---|
| | | $2^3$ | $2^4$ | $2^5$ | $2^6$ | $2^7$ | $2^8$ | $2^9$ | $2^{10}$ |
| Designation of Specimen | s-1 Ex. 3 | + | + | + | + | + | + | + | − |
| | Comp. Ex. 1 | + | + | + | + | − | − | − | − |
| | Comp. Ex. 2 | + | + | + | + | + | + | + | − |
| | s-2 Ex. 3 | + | + | + | + | + | + | − | − |
| | Comp. Ex. 1 | + | + | + | − | − | − | − | − |
| | Comp. Ex. 2 | + | + | + | + | + | + | + | − |
| | s-3 Ex. 3 | + | + | + | + | − | − | − | − |
| | Comp. Ex. 1 | + | − | − | − | − | − | − | − |
| | Comp. Ex. 2 | + | + | + | + | − | − | − | − |
| | s-4 Ex. 3 | + | + | + | + | + | + | + | − |
| | Comp. Ex. 1 | + | + | + | − | − | − | − | − |
| | Comp. Ex. 2 | + | + | + | + | + | + | − | − |
| | s-5 Ex. 3 | + | + | + | + | + | − | − | − |
| | Comp. Ex. 1 | + | + | − | − | − | − | − | − |
| | Comp. Ex. 2 | + | + | + | + | + | − | − | − |

As can be clearly seen from Table 4, the measurement results (Example 3) obtained by utilizing the immunoassay reagent of the present invention are comparable to those (Comparative Example 2) obtained by employing the commercial EIA kit, but do not show correspondences in either low- or high-concentration region to those (Comparative Example 1) obtained by utilizing the conventional latex reagent.

Example 4

(1) Reagents and Materials

Similar to those listed in "(1) Reagents and Materials" of Example 3 but excepting the followings.

Magnetizable material-containing latex: polystyrene latex (particle size of 0.4 μm, product of Belitus Co., Ltd.) containing 10% (W/V) magnetizable material ($Fe_2O_3$)

Anti human HBs antibody: goat anti human HBs antibody purified from goat antiserum to immunoglobulin fractions Anti human CRP antibody: goat anti human CRP antibody purified from goat antiserum to immunoglobulin fractions Anti-β-galactosidase monoclonal antibody: anti-β-galactosidase monoclonal antibody precipateted from ascites fluids with the aid of ammonium sulfate and purified to immunoglobulin fractions Enzyme solution (R3 solution): 1:1 mixture of anti-horseradish peroxidase (257 U/mL, product of Toyobo Co., Ltd.) diluted with the above-specified latex diluting buffer to a concentration of 0.3 U/mL and β-galactosidase (500 U/mL, product of Toyobo Co., Ltd.) diluted with the above-specified latex diluting buffer to a concentration of 0.3 U/mL.

Substrate solution (R4 solution): a mixture of 8 μL of 10 mM N-ethyl-N-(2-hydroxy-3-sulfopropyl)-3,5-dimethoxy aniline (product of Dojin Chemical Co., Ltd.), 40 μL of 4 mM 4-aminoantipyrine (product of Wako Pure Chemical Co., Ltd.) and 3 μL of 12 mM aqueous hydrogen peroxide (product of Minori Chemical Co., Ltd.), to which o-nitrophenyl-β-D-galactopyranoside was added to a concentration of 1% (W/V)

HBs standards: HBs standard (1,000 I.U./mL, 1.7 μg/mL) purified from human pool serum was diluted in physiological saline to concentrations of 400, 200, 100, 50 and 10 I.U./mL. Pure physiological saline, free of HBs standard, was used as having a concentration of 0 I.U./mL.

CRP standards: CRP standards (product of Denka Seiken Co., Ltd.) purified from human pool serum were used having concentrations of 40, 20, 10, 5 and 1 mg/dL, respectively.

Pure physiological saline, free of CRP standard, was used as having a concentration of 0 mg/dL.

Reaction terminating solution: 100 mM aqueous solution of sodium primary phosphate (2) Preparation of a Latex Reagent 2 parts by volume of latex diluting buffer was added to 1 part by volume of magnetizable material-containing polystyrene latex to obtain a 3.3% (W/V) latex solution. Anti-human HBs antibody, anti-human CRP antibody, anti-horseradish peroxidase monoclonal antibody and anti-β-galactosidase monoclonal antibody were diluted with antibody diluting buffer, respectively, to a protein concentration of 1600 μg/mL, thereby obtaining antibody solutions.

The above-prepared antibody solutions, each in the amount of 100 μL, were added quickly to 300 μL of the above-prepared 3.3% (W/V) latex solution while agitated by a magnetic stirrer in a 25° C. incubator. The mixture was agitated at 25° C. for 1 hour.

0.5 mL of blocking buffer was added to the mixture, followed by one hour of continued agitation at 25° C. This mixture was then centrifuged at 18,000 rpm at 15° C. for 20 minutes. 2 mL of blocking buffer was added to a resultant precipitate which was subsequently cleaned by centrifugation in the same manner as above. The cleaning operation was repeated three times. 2 mL of blocking buffer was added to the cleaned precipitate. After sufficient stirring, the mixture was subjected to a dispersion treatment by an ultrasonic grinder to thereby obtain a 0.25% (W/V) solids latex reagent which was subsequently stored at 4° C.

(3) Measurement Method of HBs Antigen and CRP Specimens

The immunoassay reagent of the present invention which comprises the above-prepared latex reagent (an insoluble substance that carries antigens, i.e., anti-human HBs antibody and anti-human CRP antibody, and enzyme inhibitors, i.e., anti-horseradish peroxidase monoclonal antibody and anti-β-galactosidase monoclonal antibody) and the above-specified enzyme solution and substrate solution, in combination with a spectrophotometer model # U-3200 (product of Hitachi Seisakusho Co., Ltd.), was utilized to measure human HBs and CRP specimens according to the following procedure.

The 0.25% (W/V) solids latex reagent obtained in (2) served as an R2 solution. Measurement was accomplished under the following conditions.

| Reagent loadings per specimen | |
|---|---|
| Volume of a specimen | 1 mL |
| Specimen diluting solution (R1 solution) | 1.8 mL |
| Latex reagent (R2 solution) | 0.2 mL |
| Enzyme solution (R3 solution) | 0.2 mL |
| Substrate solution (R4 solution) | 0.2 mL |
| Reaction terminating solution | 2 mL |
| Measurement wavelength | 600 nm and 420 nm |
| Measurement temperature | 37° C. |

A sequence used to introduce the reagents into the specimen loaded cell of the above-specified autoanalyzer comprises introducing R1 solution, R2 solution three minutes later, R3 solution ten minutes later, R4 solution ten minutes later and reaction terminating solution ten minutes later. After introduction of the reaction terminating solution, a magnet was manipulated to attract magnetizable material-containing latex particles to a bottom of the specimen cell where they were caused to settle. The absorbency of a resultant supernatant was measured both at 600 nm and 420 nm.

An absorbency change at a wavelength of 600 nm was given by subtracting an absorbency value measured for the specimen consisting solely of physiological saline from an absorbency value measured for each of the standard specimens having the below-specified HBs concentrations.

An absorbency change at a wavelength of 420 nm was given by subtracting an absorbency value measured for the specimen consisting solely of physiological saline from an absorbency value measured for each of the standard specimens having the below-specified CRP concentrations.

(4) Measurement Results

The HBs standard and CRP standard as specified in the section of Reagents and Materials were used to prepare the below-described standard specimens containing different concentrations of HBs and CRP standards.

The standard specimens respectively contained 0 I.U./mL of HBs standard and 0 mg/dL of CRP standard (i.e., contained physiological saline only); 10 I.U./mL of HBs standard and 1 mg/dL of CRP standard; 50 I.U./mL of HBs standard and 5 mg/dL of CRP standard; 100 I.U./mL of HBs standard and 10 mg/dL of CRP standard; and 200 I.U./mL of HBs standard and 20 mg/dL of CRP standard.

The above-described procedure (3) was followed to measure an absorbency change for the standard specimens containing different concentrations of HBs and CRP standards. The relationships between the absorbency change (at 600 nm) and the HBs standard concentration (I.U./mL) and between the absorbency change (at 420 nm) and the CRP standard concentration (mg/dL) were respectively shown in Table 5.

TABLE 5

| | | | | |
|---|---|---|---|---|
| Concentration of HBs Standard (IU/mL) | 10 | 50 | 100 | 200 |
| Absorbency Change (600 nm) | 0.118 | 0.601 | 1.211 | 2.43 |
| Concentration of CRP Standard (mg/dL) | 1 | 5 | 10 | 20 |
| Absorbency Change (420 nm) | 0.101 | 0.214 | 1.041 | 2.112 |

A calibration curve was constructed using the results given in Table 5.

Next, three different serum specimens (designated as A, B and C) were measured for absorbency change according to the above-described procedure (3). The absorbency change obtained for each serum specimen was then applied onto the calibration curve to thereby determine its HBs and CRP concentrations. The results are given in Table 6.

TABLE 6

| Designation of Specimen | HBs Concentration (IU/mL) | CRP Concentration (mg/dL) |
|---|---|---|
| A | 24 | 1.2 |
| B | 58 | 2.3 |
| C | 133 | 4.1 |

It has been recognized from these results that the immunoassay reagent and method according to the present invention are capable of being used for many different types of specimens and allow the simultaneous assay of different substances in a simple fashion.

Example 5
(1) Preparation of a Reagent

20 µl of an SMCC (N-succinimidyl-4-(N-maleimidomethyl)-1-carboxylate) solution in dimethylformamide at a concentration of 4 mg/ml was added to 1 ml of an anti-β-galactosidase antibody (rabbit derived polyclonal antibody) IgG solution in water at a concentration of 1 mg/ml. The mixture was stirred at 30° C. for 10 minutes so that anti-β-galactosidase antibody was bound to SMCC.

The resultant solution was diluted with 0.1 M phosphate buffer (pH 7.0) to a total volume of 10 ml and then gel filtered through a Pharmacia PD-10 column. An initial 3 ml fraction was thrown away and the following 1.5 ml fraction was dispensed, so that SMCC-linked anti-β-galactosidase antibody (maleimide-bound anti-β-galactosidase antibody) was extracted.

Next, 0.1 mg of HCV (hepatitis C virus) C-100 antigen protein was added to the above-dispensed 1.5 ml fraction of maleimide-linked anti-β-galactosidase antibody. The mixture was stirred at 30° C. for 60 minutes to produce a conjugate of HCV C-100 antigen protein and anti-β-galactosidase antibody, which served as a reagent 1.

Then, 10 ml of β-galactosidase dissolved in 0.1 M phosphate buffer (pH 7.0) at a concentration of 1 mg/ml was prepared for use as a reagent 2.

Also, 10 ml of o-nitrophenyl-β-D-galactopyranoside (ONPG) dissolved in 0.1 M phosphate buffer (pH 7.0) at a concentration of 0.1 weight % was prepared for use as a reagent 3.

That is, the immunoassay reagent according to this Example consists of the aforementioned reagent 1 (antigen chemically linked to anti-β-galactosidase antibody as an enzyme inhibitor), reagent 2 (enzyme whose activity is to be inhibited by the enzyme inhibitor) and reagent 3 (substrate with which the enzyme reacts).

(2) Assaying

Specimens A, B and C from hepatitis C patients and other specimens consisting of standard serums 0, 1, 2, 4, 8, 16 COIs (Cut Off Index) were prepared. 100 µl of each specimen was mixed with 100 µl of reagent 1 and left to stand at 37° C. for 10 minutes, then mixed with 200 µl of reagent 2 and left to stand at 37° C. for 10 minutes, and finally mixed with 1,000 µl of reagent 3 and left to stand at 37° C. for 10 minutes. Thereafter, an absorbency at 420 nm was measured. A calibration curve was constructed using absorbency values obtained for standard specimens and their COIs. Absorbency values obtained for the specimens A, B and C were applied onto the calibration curve to find their respective COIs. As a result, the specimens A, B and C were found as being 8 COI, 4 COI and 5 COI, respectively.

Example 6
(1) Reagent Preparation

20 µl of an SMCC solution in dimethylformamide at a concentration of 4 mg/ml was added to 1 ml of an anti-β-galactosidase monoclonal antibody IgG solution in water at a concentration of 1 mg/ml. The mixture was stirred at 30° C. for 10 minutes so that the anti-β-galactosidase antibody was bound to SMCC.

The resultant solution was diluted with 0.1 M phosphate buffer (pH 7.0) to a total volume of 10 ml and then gel filtered through a Pharmacia PD-10 column. An initial 3 ml fraction was thrown away and the following 1.5 ml fraction was dispensed, so that SMCC-linked anti-β-galactosidase antibody (maleimide-linked anti-β-galactosidase antibody) was extracted.

Next, 0.1 mg of HCV (hepatitis C virus) C-100 antigen protein was added to the above-dispensed 1.5 ml fraction of maleimide-linked anti-β-galactosidase antibody. The mixture was stirred at 30° C. for 60 minutes to produce a conjugate of HCV C-100 antigen protein and anti-β-galactosidase antibody, which served as a reagent 1.

Then, 10 ml of β-galactosidase dissolved in 0.1 M phosphate buffer (pH 7.0) at a concentration of 1 mg/ml was prepared for use as a reagent 2.

Also, 10 ml of o-nitrophenyl-β-D-galactopyranoside dissolved in 0.1 M phosphate buffer (pH 7.0) at a concentration of 0.1 weight % was prepared for use as a reagent 3.

That is, the immunoassay reagent according to this Example consists of the aforementioned reagent 1 (antigen chemically linked to anti-β-galactosidase monoclonal antibody as an enzyme inhibitor), reagent 2 (enzyme whose activity is to be inhibited by the enzyme inhibitor) and reagent 3 (substrate with which the enzyme reacts).

(2) Assaying

Specimens D, E and F from hepatitis C patients and other specimens consisting of standard serums 0, 1, 2, 4, 8, 16 COIs (Cut Off Index) were prepared. 100 µl of each specimen was mixed with 100 µl of reagent 1 and left to stand at 37° C. for 10 minutes, then mixed with 200 µl of reagent 2 and left to stand at 37° C. for 10 minutes, and finally mixed with 1,000 µl of reagent 3 and left to stand at 37° C. for 10 minutes. Thereafter, an absorbency at 420 nm was measured. A calibration curve was constructed using absorbency values obtained for standard specimens and their COIs. Absorbency values obtained for the specimens D, E and F were applied onto the calibration curve to find their respective COIs. As a result, the specimens D, E and F were found as being 2 COI, 15 COI and 9 COI, respectively.

EFFECTS OF THE INVENTION

The Immunoassay reagent in accordance with the first invention of the present application contains (a) an insoluble carrier that carries an antibody or antigen and an enzyme, (b) an enzyme inhibitor and (c) a substrate. When this immunoassay reagent is mixed with a sample, an antigen-antibody reaction in the form of agglutination reaction of the insoluble carriers, as well as the enzyme reaction, are caused to occur. By measuring the degrees of these reactions, a microscale substance in the sample, such as the antigen or antibody, can be quantitated at high sensitivity. Also, the absence of a B/F separation simplifies the assay.

The Immunoassay reagent in accordance with the second invention contains (a) an insoluble carrier that carries an antibody or antigen and an enzyme inhibitor, (b) an enzyme and (c) a substrate. When this immunoassay reagent is mixed with a sample, an antigen-antibody reaction in the form of agglutination reaction of the insoluble carriers, as well as an enzyme reaction, are also caused to occur. By measuring the degrees of these reactions, a microscale substance in the sample, such as antigen or antibody, can be quantitated at high sensitivity. Also in the second invention, a B/F separation is not required or can be simplified. This simplifies the assay.

The Immunoassay reagent in accordance with the third invention contains (a) an antibody or antigen chemically linked to an enzyme inhibitor, (b) an enzyme and (c) a substrate. When this immunoassay reagent is mixed with a sample, an antigen-antibody reaction and an enzyme reaction are caused to occur. By measuring the degrees of these reactions, a microscale substance in the sample, such as the antigen or antibody, can be quantitated at high sensitivity.

Also in the case of using the immunoassay reagent according to the third invention, a B/F separation is not required or can be simplified. This simplifies the assay.

The immunoassay method in accordance with the present invention, can quantitate a microscale substance in a sample, such as antigen or antibody, with high sensitivity, because of its use of the reagent according to the first, second or third invention, and can be carried out in a simple manner because it does not need or can simplify a B/F separation.

What is claimed is:

1. An immunoassay reagent for use in a quantitative determination of a target antigen or antibody present in a sample, said reagent consisting essentially of the following components:
   (a) an insoluble carrier which carries and is coupled to an enzyme and an antibody or antigen reactive with said target antigen or antibody, said insoluble carrier comprising at least one selected from the group consisting of an organic polymer powder particle, microorganism, blood cell and cell membrane fragment, said insoluble carrier being capable of aggregation;
   (b) an enzyme inhibitor for reacting with and inhibiting activity of said enzyme, said enzyme inhibitor being in a free state uncoupled to an antigen or antibody and being increasingly hindered from reacting with said enzyme when said insoluble carrier is increasingly agglutinated; and
   (c) a substrate for the enzyme capable of producing an optically detectable indication of reaction with the enzyme, wherein said substrate is not hindered from reacting with said enzyme when said enzyme is unreacted with said enzyme inhibitor when said insoluble carrier is increasingly aggregated, said components (a)–(c) being maintained separate and apart and mixed together only with a sample containing the target antigen or antibody.

2. The immunoassay reagent of claim 1, wherein said insoluble carrier further contains a magnetic or magnetizable material.

3. The immunoassay reagent of claim 1, wherein said enzyme inhibitor is an antibody against said enzyme.

4. The immunoassay reagent as recited in claim 3, wherein said antibody against the enzyme is a monoclonal antibody.

5. An immunoassay method for quantitatively determining a target antigen or antibody present in a sample, comprising:
   first mixing the immunoassay reagent of claim 1 with the sample to thereby facilitate an enzyme reaction and an antigen-antibody reaction resulting in agglutination of the insoluble carrier to form a mixture; and
   then measuring the absorbance of said mixture as an index of an amount of target antigen or antibody in the sample.

6. An immunoassay reagent for use in a quantitative determination of a target antigen or antibody present in a sample, said reagent consisting essentially of the following components:
   (a) an insoluble carrier which carries and is coupled to an enzyme and an antibody or antigen reactive with said target antigen or antibody, said insoluble carrier comprising at least one selected from the group consisting of an organic polymer powder particle, microorganism, blood cell and cell membrane fragment, said insoluble carrier being capable of aggregation;
   (b) an enzyme inhibitor for reacting with and inhibiting activity of said enzyme, said enzyme inhibitor being in a free state uncoupled to an antigen or antibody and being increasingly hindered from reacting with said enzyme once said insoluble carrier is increasingly agglutinated; and
   (c) a substrate for the enzyme capable of producing an optically detectable indication of reaction with the enzyme, wherein said substrate is not hindered from reacting with said enzyme when said enzyme is unreacted with said enzyme inhibitor when said insoluble carrier is increasingly aggregated, said immunoassay reagent consisting of a first reagent and a second reagent, wherein said first reagent contains said insoluble carrier and said second reagent contains said enzyme inhibitor and said substrate.

7. An immunoassay reagent for use in quantitative determination of a target antigen or antibody present in a sample, said reagent consisting essentially of the following components:
   (a) an insoluble carrier which carries and is coupled to an enzyme inhibitor and an antibody or antigen reactive with said target antigen or antibody, said insoluble carrier comprising at least one selected from the group consisting of an organic polymer powder particle, microorganism, blood cell and cell membrane fragment, said insoluble carrier being capable of aggregation;
   (b) an enzyme which reacts with and whose enzymatic activity is inhibited by said enzyme inhibitor, said enzyme being in a free state uncoupled to an antigen or antibody and being increasingly sterically hindered from reacting with said enzyme inhibitor when said insoluble carrier is increasingly aggregated; and
   (c) a substrate for the enzyme capable of producing an optically detectable indication of reaction with the enzyme;
   said components (a)–(c) being maintained separate and apart and sequentially mixed together only with a sample of target antigen or antibody, the addition of the substrate facilitating reaction with the enzyme, thereby effecting an optically detectable change in absorbence.

8. The immunoassay reagent of claim 7, wherein said insoluble carrier further contains a magnetic or magnetizable material.

9. The immunoassay reagent of claim 7, wherein said enzyme inhibitor is an antibody against said enzyme.

10. The immunoassay reagent as recited in claim 9, wherein said antibody against the enzyme is a monoclonal antibody.

11. An immunoassay method for quantitatively determining a target antigen or antibody present in a sample, comprising:
    sequentially mixing said components (a)–(c) of the immunoassay reagent of claim 3 with a sample suspected of containing a quantity of said target antigen or antibody, wherein a plurality of said insoluble carrier carrying said antibody or antigen reactive with said target antigen or antibody, respectively, are first mixed with the sample under conditions sufficient for a level of agglutination of the carriers when said target antigen or antibody is present in the sample,
    thereafter adding said component (b) to the mixed sample under conditions sufficient for the enzyme to react with said carrier-coupled enzyme inhibitor to a level dependent upon steric hindrance dependent upon the level of agglutination of the carriers,
    thereafter adding the enzyme substrate to react with the enzyme which has not reacted with the enzyme inhibitor to produce a level of optically detectable signal, and optically determining the level of signal as an indication of the level of agglutination of the carriers indicative of the quantity of the target antigen or antibody in the sample.

* * * * *